(12) United States Patent
Staehler et al.

(10) Patent No.: US 11,399,871 B2
(45) Date of Patent: Aug. 2, 2022

(54) BONE DISTRACTION DEVICE HAVING A QUICK RELEASE DISENGAGEMENT MECHANISM

(71) Applicant: Wendy L. Johnston, Jacksonville, FL (US)

(72) Inventors: Heinz Staehler, Mulheim (DE); Thomas S. Johnston, Jr., Jacksonville, FL (US)

(*) Notice: Subject to any disclaimer, the term of this patent is extended or adjusted under 35 U.S.C. 154(b) by 517 days.

(21) Appl. No.: 16/448,340

(22) Filed: Jun. 21, 2019

(65) Prior Publication Data

US 2020/0069336 A1     Mar. 5, 2020

Related U.S. Application Data

(60) Provisional application No. 62/688,130, filed on Jun. 21, 2018.

(51) Int. Cl.
| | |
|---|---|
| *A61B 17/66* | (2006.01) |
| *A61B 17/70* | (2006.01) |
| *A61B 17/64* | (2006.01) |
| *A61B 17/80* | (2006.01) |
| *A61B 17/68* | (2006.01) |
| *A61B 17/00* | (2006.01) |

(52) U.S. Cl.
CPC ........ *A61B 17/663* (2013.01); *A61B 17/6475* (2013.01); *A61B 17/7008* (2013.01); *A61B 17/8019* (2013.01); *A61B 2017/00407* (2013.01); *A61B 2017/681* (2013.01)

(58) Field of Classification Search
CPC ..... A61B 17/66; A61B 17/666; A61B 17/663; A61B 17/8009; A61B 17/8004; A61B 17/8014; A61B 17/8019
See application file for complete search history.

(56) References Cited

U.S. PATENT DOCUMENTS

| | | |
|---|---|---|
| 1,981,698 A | 11/1932 | Henning |
| 5,681,309 A | 10/1997 | Ross, Jr. et al. |
| 5,704,938 A | 1/1998 | Staehlin et al. |
| 5,807,382 A | 9/1998 | Chin |

(Continued)

FOREIGN PATENT DOCUMENTS

| | | | | |
|---|---|---|---|---|
| DE | 102010015687 A1 | * 10/2011 | .......... | A61C 8/0006 |
| WO | WO-2008129995 A1 | * 10/2008 | ......... | A61B 17/7216 |

OTHER PUBLICATIONS

Machine Enlgish Translation of DE-102010015687-A1 via espacenet.com, printed on Dec. 4, 2021.*

*Primary Examiner* — Jan Christopher L Merene
(74) *Attorney, Agent, or Firm* — Thomas C. Saitta

(57) ABSTRACT

A bone distraction device having a ratchet and pawl assembly such that incremental rotation is allowed in one direction and prevented in the other, and further having a quick release mechanism such that the ratchet and pawl mechanism can be released to allow free rotation in both directions. The device has a pawl housing mounted onto a rod housing, the pawl housing having a sloping transition shoulder diminishing to transition onto the outer surface of the rod housing. In other embodiments, the device has a sleeve housing with an enlarged end telescopically mounted onto a rod housing, the enlarged end having a sloping transition shoulder diminishing to transition onto the outer surface of the sleeve housing.

9 Claims, 6 Drawing Sheets

(56) References Cited

U.S. PATENT DOCUMENTS

| | | | |
|---|---|---|---|
| 5,855,580 A * | 1/1999 | Kreidler | A61B 17/663 606/71 |
| 5,928,231 A | 7/1999 | Klein et al. | |
| 6,033,412 A | 3/2000 | Losken et al. | |
| 6,277,124 B1 | 8/2001 | Haag | |
| 6,423,069 B1 * | 7/2002 | Sellers | A61B 17/663 606/71 |
| 6,752,808 B2 | 6/2004 | Schumacher | |
| 2005/0234448 A1 | 10/2005 | McCarthy | |
| 2005/0256526 A1 * | 11/2005 | Johnston | A61B 17/663 606/282 |
| 2006/0079902 A1 | 4/2006 | Johnston | |
| 2010/0076444 A1 | 3/2010 | Staehler et al. | |
| 2012/0259344 A1 * | 10/2012 | Johnston, Jr. | A61B 17/8004 606/105 |
| 2016/0058485 A1 | 3/2016 | Staehler et al. | |
| 2016/0120580 A1 * | 5/2016 | Johnston, Jr. | A61B 17/663 606/282 |
| 2019/0209211 A1 * | 7/2019 | Charest | A61B 17/7014 |
| 2021/0085377 A1 * | 3/2021 | Johnston, Jr. | A61B 17/663 |

\* cited by examiner

BONE DISTRACTION DEVICE HAVING A QUICK RELEASE DISENGAGEMENT MECHANISM

BACKGROUND OF THE INVENTION

This invention relates generally to the field of medical distraction devices in the field of bone fixation, repair and regeneration, and more particularly relates to such devices and methods utilized in mandibular and maxillary craniofacial repair, facial reconstruction, and treatment for congenital, developmental and traumatic defects.

It is often desirable or necessary to effect reconstruction or repair of the craniofacial bones defining the face of a person, such as the midface, the mandible and/or the maxilla. This need may arise from congenital conditions, developmental disorders or trauma. In many circumstances the abnormalities are corrected by first dividing a bone through osteotomy, i.e., cutting or fracturing a bone to create two segments separated by a gap or space. In some instances the bone segments will be shifted into the proper orientation and alignment, and then fixed in place relative to each other until bone growth across the gap results in the formation of a unitary bone member. In other instances it is necessary to lengthen the original bone member, in which case devices known as distractors are utilized. A distractor is a device that has affixation means, such as bone plates, that are joined to each of the bone segments on opposite sides of the osteotomy using mechanical fasteners such as bone screws. The device further includes distraction means that allows the distance between the bone plates to be slowly increased over time, thereby allowing new bone growth to occur between the bone segments. The distraction means may comprise for example a threaded rod contained within a framework or elongated housing, the rod being in connection with one or two translatable shoe or mounting members to which are connected a proximal bone plate and a distal bone plate, whereby the bone plates affixed on either side of the osteotomy gap to the bone to be extended can be gradually separated in a controlled and precise manner by rotating the threaded rod to separate the plate mounting members. The new bone growth increases in dimension until the proper bone length is achieved, at which time the distraction process is halted and the distractor is removed. U.S. Pat. No. 6,752,808 issued to Schumacher illustrates and describes a distraction device of the type referenced above.

A typical example of this procedure is when the mandible or jawbone fails to fully develop in the anterior-posterior direction, a condition known as mandibular hypoplasia, which is manifested as a severely fore-shortened chin. To correct this anomaly, osteotomies are performed on each side of the mandible and a pair of distraction devices are affixed to the mandible. Extension of the distractors is performed in unison to lengthen the mandible until the desired position of the mandible relative to the midface is achieved. After sufficient regeneration and healing, the distractors are removed.

For another example, it is often desired to advance the midface or maxillary region relative to the jaw and skull to correct for maxillary hypoplasia, where the upper lip and/or nose are depressed relative to the remainder of the face structure. In this case the osteotomy may be performed across the maxilla to the nasal cavity, and a pair of distractors are affixed across the osteotomy gap, or an external distraction apparatus is mounted to the skull with affixed means to distract the anterior maxillary segment. Gradual extension of the distractors in unison advances the anterior maxillary segment relative to the posterior maxillary segments while bone regeneration fills in the osteotomy gap. When the proper position is achieved, distraction is halted. After sufficient regeneration and healing, the distractors are removed.

It is desirable that the distraction be performed in a controlled or incremental manner, whereby the advancement distance can be accurately accounted for, and it is further desirable that the apparatus allow for rotation in only one direction to insure that the bone plates are separated rather than contracted. This may be accomplished by utilizing a ratchet and pawl mechanism or having mating teeth, such that rotation of the drive head joined to the threaded rod and relative movement of the bone plates can only occur in the distraction direction. Examples of distraction devices utilizing ratchet and pawl mechanisms or mating teeth are seen in U.S. Pat. No. 5,681,309 to Ross, Jr. et al., U.S. Pat. No. 5,704,938 to Stawhlin et al., U.S. Pat. No. 6,033,412 to Losken et al., and U.S. Pat. No. 6,277,124 to Haag.

One problem with such unidirectional distraction devices is that it may be desirable or required to contract the bone plates by rotating the threaded drive rod in the direction opposite to the distraction direction. In certain circumstances, it may be necessary to allow for free rotation of the threaded drive rod rather than incremental rotation. It may also be necessary in certain circumstances to release the threaded drive rod quickly. To address this it is known to provide a distraction device having a ratchet and pawl means that allows for incremental rotation of the threaded drive rod in the distraction direction, wherein a quick release disengagement means is provided such that the ratchet and pawl mechanism can be disengaged and the drive rod rotated in the opposite direction as needed, such as shown in U.S. Pat. No. 5,681,309 to Ross, and in U.S. Pat. Appl. Publ. 2016/0058485 to Staehler et al. (the Staehler reference).

The prior art Staehler reference is illustrated in FIGS. 1 through 3 of this application. FIG. 1 illustrates a representative embodiment of the distraction device comprising a distraction mechanism for separating a pair of bone portions divided by an osteotomy, the distraction device comprising structures for affixing the device to bone on either side of the osteotomy gap, such as for example a pair of bone plate members 11, the bone plate members 11 having apertures 12 to receive mechanical fasteners such as bone screws, as is well known in the art. The distraction mechanism comprises a threaded rod 13 received within a framework or elongated, linear rod housing 14 in a manner whereby the threaded rod 13 may be rotated by turning a drive head member 15 coaxially mounted on one end of the housing 14. One of the bone plate members 11 is fixedly mounted to the rod housing 14 and the other bone plate member 11 is mounted to the threaded rod 13 such that an apertured portion of each bone plate member 11 extends from each side of the threaded rod 13, and in a manner whereby rotation of the threaded rod 13 causes the bone plates 11 to separate or contract relative to each other, such as for example by utilizing an internally threaded mounting member or shoe (not shown) on one of the bone plate members 11 that receives the threaded rod 13, the mounting member being able to move longitudinally along the housing 14 when the threaded rod 13 is rotated. Such mechanisms are well known in the art. Typically, the drive head member 15 is provided with a drive tool receiving bore or slot, such that rotation of the threaded rod 13 is achieved by inserting the drive tool, such as for example a hexagonal shaft, into the bore and rotating the drive tool.

The distraction device further comprises an incremental indexing mechanism to rotate the drive head 15 and threaded rod 13 in a single direction via a ratchet and pawl assembly 20 that interacts with ratchet teeth 28 and notches 21 provided annularly on the drive head member 15. The pawl member 22 is provided with a curved or angled end 23 and is biased outwardly against the ratchet notches 21 by a spring or biasing member 24. The pawl 22 is retained within a pawl housing 25 mounted on the rod housing 14 adjacent the drive head member 15. In this manner, the drive head 15 can be rotated in one direction relative to the housing 14, with the rotation resulting in the depression of the biasing member 24 into the pawl housing 25 because of the angled or curved end 23. When the drive head 15 brings the next notch 21 in alignment with the pawl 22, the biasing member 24 forces the pawl 22 outward, locking the drive head 15 in position until further rotation force is applied because the extended portion of the pawl end 23 opposite from the angle or curve abuts the side of the teeth 28, precluding rotation in the opposite direction. This structure results in separation of the bone plate members 11 by a defined distance with each turn of the drive head 15. In an alternative embodiment, as shown in FIG. 3, the notches 21 may be provided with a curved or angled wall and the pawl end 23 presented as generally rectangular or cylindrical, in known manner, such that as before the drive head 15 can be rotated in only one direction when the pawl 22 is engaged, which in this figure is shown opposite to the direction of FIG. 2.

The distraction device further comprises a disengagement mechanism for releasing the ratchet and pawl mechanism such that the drive head 15 can be freely rotated in either direction. The disengagement mechanism comprises an L-shaped slot 26 disposed in the pawl housing 25 and a radially extending post member 27 that is mounted on the pawl 22 and extends through the L-shaped slot 26. To completely disengage the pawl 22 from the drive head 15, the post member 27 is moved longitudinally within the slot 26 to depress the biasing member 24 and retract the pawl 22 a sufficient distance such that it does not contact the notches 21. The post member 27 is then moved circumferentially into the annularly oriented portion of the L-shaped slot 26 to preclude the post member 27 from being advanced outwardly by the biasing member 24. In this disengaged state, the drive head 15 can now be freely rotated in either direction such that the bone plate members 11 can be contracted or distracted as needed. To engage the pawl 22, the post member 27 is simple moved from the annularly oriented portion of the L-shaped slot 26 back into the position where the biasing member 24 can push it and the pawl longitudinally within the slot 26, thereby extending the pawl end 23 into one of the notches 21 of the drive head 15. Alternatively, the slot 26 can be linear, such that the post member 27 must be held in the retracted position to allow for free rotation of the drive head 15 in either direction.

A problem inherent in the known distraction devices of the type illustrated by the Staehler reference is that the distraction devices present exposed edges and transitions having right angle junctions. Because the devices are inserted and implanted into soft tissue, these exposed edges and transitions may result in damage to the tissue during insertion, during the distraction procedure, or during removal of the distraction device. It is an object of this invention to provide a distraction device having sloping or curved edges and transitions, such that movement of portions of the device during implantation, distraction or removal are less likely to damage soft tissue.

SUMMARY OF THE INVENTION

The invention is a bone distractor, and is especially drawn to a bone distractor used in mandibular and maxillary craniofacial repair, reconstruction and treatment that enables a surgeon to lengthen the maxilla or the mandible. In a representative use, osteotomies are provided on the left and right sides of the mandible or the maxilla (or both), such that the anterior portion of the mandible or the maxilla is divided from the posterior portion. This allows the anterior portions to be repositioned in a more desirable orientation.

The bone distractor of the invention comprises means for attachment of the device to a bone on opposite sides of an osteotomy gap, such as by a pair of bone plate members affixed by bone screws or similar bone attachment members known in the art. The bone distractor further comprises distraction means to separate the bone plates, such that the bone portions to which the device is attached are gradually separated as well, such as by a threaded rod retained within an elongated framework or rod housing, such that rotation of the threaded rod results in separation movement of one or both of the bone plates. The bone distractor device further comprises a ratchet and pawl mechanism or assembly whereby rotation of the threaded rod by means of a tool inserted into a drive head is allowed in only one direction while the pawl is engaged, the pawl serving to secure the threaded rod in incremental positions relative to the rod housing, and further comprising disengagement means whereby the pawl can be quickly and easily retracted and the ratchet released such that free rotation of the threaded rod in either direction is possible so as to be able to contract the bone plates. In one embodiment the bone distractor further comprises a pawl housing for the release actuator member which extends outwardly from the rod housing, the pawl housing having a sloping transition shoulder extending down to the outer surface of the rod housing. In another embodiment the bone distractor comprises a sleeve housing disposed about the rod housing, with one bone plate affixed to the sleeve housing, the sleeve housing comprising an enlarged proximal end defining a receptacle configured to encompass the pawl housing when the distractor is in its fully contracted state, the enlarged end having a sloping transition shoulder joining the enlarged end to the outer surface of the sleeve housing.

In alternative summary, the invention is a bone distraction device comprising a pair of bone plate members; a threaded rod retained within an elongated, linear rod housing having an outer surface, whereby rotation of said threaded rod within said rod housing in a distraction direction results in relative separation of said bone plate members and rotation of said threaded rod in the opposite direction results in relative contraction of said bone plate members; a drive head positioned at one end of said rod housing and connected to said threaded rod, whereby rotation of said drive head rotates said threaded rod, said drive head having teeth and notches disposed annularly thereon; a pawl housing positioned on and extending outwardly from said rod housing, said pawl housing retaining a pawl biased into one of said notches on said drive head to define an engaged position, said pawl and said notches configured such that said drive head is rotatable only in said distraction direction when said pawl is in said engaged position; said pawl housing comprising a sloping transition shoulder diminishing to transition onto said outer surface of said rod housing; a slot disposed in said pawl housing and a post member connected to said pawl and extending through said slot, said slot having a longitudinal portion and an annularly oriented portion, and whereby said pawl is retracted away from said drive head notches and teeth by moving said post member within said slot longitudinally away from said drive head and then annularly to define a disengaged position, such that rotation of said drive head is allowable in either direction when said pawl is in said disengaged position. Furthermore, said rod housing having a proximal end and a distal end, wherein said drive head is positioned on said proximal end of said rod housing and said pawl housing is positioned on said distal end of said rod housing, wherein said sloping transition shoulder diminishes in the proximal direction; and/or said rod housing having a proximal end and a distal end, wherein said drive head and said pawl housing are positioned on said proximal end of said rod housing, wherein said sloping transition shoulder diminishes in the distal direction.

Alternatively summarized, the invention is a bone distraction device comprising a pair of bone plate members; a threaded rod retained within an elongated, linear rod housing having an outer surface; a drive head positioned at one end of said rod housing and connected to said threaded rod, whereby rotation of said drive head rotates said threaded rod, said drive head having teeth and notches disposed annularly thereon; a pawl housing positioned on and extending outwardly from said rod housing adjacent said drive head, said pawl housing retaining a pawl biased into one of said notches on said drive head to define an engaged position, said pawl and said notches configured such that said drive head is rotatable only in one direction when said pawl is in said engaged position; a slot disposed in said pawl housing and a release actuation member connected to said pawl and extending through said slot, said slot having a longitudinal portion and an annularly oriented portion, and whereby said pawl is retracted away from said drive head notches and teeth by moving said post member within said slot longitudinally away from said drive head and then annularly to define a disengaged position, such that rotation of said drive head is allowable in either direction when said pawl is in said disengaged position; a sleeve housing telescopically mounted on said rod housing, wherein one of said pair of bone plate members is affixed to said rod housing and the other of said pair of bone plate members is affixed to said sleeve housing; whereby rotation of said threaded rod within said rod housing in the distraction direction results in lengthening of said bone distraction device and relative separation of said bone plate members and rotation of said threaded rod in the opposite direction results in shortening of said bone distraction device and relative contraction of said bone plate members. Furthermore, said rod housing having a proximal end and a distal end, wherein said drive head and said pawl housing are positioned on said proximal end of said rod housing; said sleeve housing having a proximal end and a distal end, said sleeve housing further comprising an enlarged end at the proximal end of said sleeve housing, said enlarged end comprising a pawl housing recess sized and configured to receive said pawl housing therein; said enlarged end of said sleeve housing further comprising a release actuation notch such that said release actuator remains accessible when said pawl housing is received within said pawl housing recess; said enlarged end comprising a sloping transition shoulder diminishing to transition onto said outer surface of said sleeve housing in the distal direction; and/or said pawl housing comprising a sloping transition shoulder diminishing to transition onto said outer surface of said rod housing in the distal direction.

DETAILED DESCRIPTION OF THE INVENTION

Figure 1:
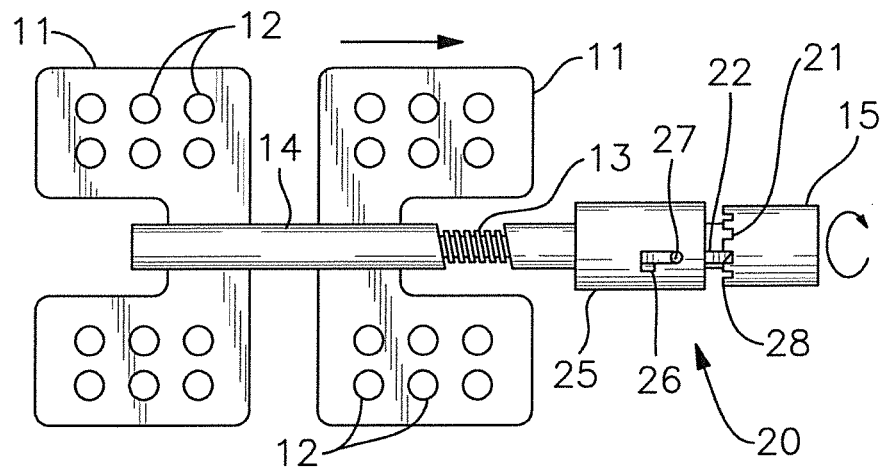
FIG. 1 is a plan view of a prior art unidirectional distraction device having a quick release disengagement mechanism.

With reference to the drawings, the invention will now be described in detail with regard for the best mode and the preferred embodiments. The invention is a bone distractor, and is especially drawn to a bone distractor used in mandibular and maxillary craniofacial repair, reconstruction and treatment. In a representative procedure, osteotomies are provided on the left and right sides of the mandible or the maxilla, such that the anterior portion of the bone is divided from the posterior portion of the bone. A pair of distractor devices are utilized, one for each side of the mandible or maxilla. The distractor device is affixed to the mandible or maxilla spanning the osteotomy gap. Distraction is accomplished slowly to allow bone regeneration to occur across the osteotomy gap. When the bones are properly lengthened, the device is removed.

FIGS. 4 through 7 illustrate a representative embodiment of a first embodiment of the distraction device comprising distraction means for separating a pair of bone portions divided by an osteotomy, the distraction device comprising means for affixing the device to bone on either side of the osteotomy gap, such as for example a pair of bone plate members 111, the bone plate members 111 having apertures 112 to receive mechanical fastener means such as bone screws, as is well known in the art. The distraction means preferably comprises an internal threaded rod (not shown) of the type known in the prior art which is received within a framework or elongated rod housing 114 in a manner whereby the threaded rod may be rotated by turning a drive head member 115 to separate the bone plate members 111. One or both of the bone plate members 111 are mounted to the threaded rod in a manner whereby rotation of the threaded rod causes the bone plates 111 to separate or contract relative to each other, such as for example by utilizing an internally threaded mounting member or shoe (not shown) on one of the bone plate members 111 that receives the threaded rod, the mounting member being able to move longitudinally along the rod housing 114 when the threaded rod is rotated. Such mechanisms are well known in the art. Typically, the drive head member 115 is provided with a drive tool receiving bore or slot 113, such that rotation of the threaded rod is achieved by inserting the drive tool, such as for example a hexagonal shaft, into the bore 113 and rotating the drive tool.

The distraction device further comprises incremental indexing means for allowing rotation of the drive head 115 and threaded rod in a single direction via a ratchet and pawl mechanism or assembly 120 that interacts with non-symmetrical ratchet teeth 128 and notches 121 disposed on a ratchet head 123. The ratchet teeth 128 are configured such that one side of each tooth 128 extends longitudinally with an angled surface or contact edge while the other side of the tooth 128 presents a longitudinally extending edge coaxially aligned. The ratchet and pawl assembly 120 in this embodiment is disposed on the distal end of the rod housing 114 and the drive head member 115 is disposed on the proximal end of the rod housing 114. As used herein, the term proximal shall be taken to refer to the direction toward the drive head member 115, with the term distal referring to the opposite direction along the distraction device.

The drive head 115 and the ratchet head 123 are connected by the threaded rod. The pawl member 122 is preferably provided with a curved end and is biased outwardly against the ratchet notches 121 by a biasing member (not shown). The pawl is retained within a pawl housing 125 mounted on the rod housing 114, the pawl housing having a rounded, curved or sloping transition shoulder 129 which diminishes in the proximal direction, i.e., the direction toward the drive head member 115 so as to contact the outer surface of the rod housing 114. In this manner, the drive head 115 can be rotated in the distraction direction to rotate the ratchet head 123, the rotation resulting in the depression of the biasing member into the pawl housing 125 due to cam-like movement of the angled contact surface of the teeth 128. When the drive head 115 brings the next notch 121 on the ratchet head 123 in alignment with the pawl 122, the biasing member forces the pawl member 122 outwardly into the notch 121, locking the drive head 115 in position until further rotation force is applied because the extended portion of the pawl end abuts the straight side of the teeth 128, precluding rotation in the opposite direction, i.e., the direction that would bring the bone plates 111 together rather than apart. This structure results in separation of the bone plate members 111 by a defined distance with each turn.

The distraction device further comprises disengagement means for releasing the ratchet and pawl mechanism 120 such that the drive head 115 can be freely rotated in either direction. The disengagement means preferably comprises an L-shaped slot 126 disposed in the pawl housing 125 and a radially extending release actuator 127, such as a post member that is mounted on the pawl 122 and extends through the L-shaped slot 126. To disengage the pawl from the ratchet head 123, the post member 127 is moved longitudinally within the axial portion of the slot 126 to depress the biasing member and retract the pawl a sufficient distance such that it does not contact the notches 121. The post member 127 is then moved circumferentially into the circumferential portion of the L-shaped slot 126 to preclude it from being advanced outwardly by the biasing member. In this disengaged state, the drive head 115 can now be rotated in either direction such that the bone plate members 111 can be either contracted or distracted. To engage the pawl, the post member 127 is simple moved back into the axial portion of the slot 126 where the biasing member can push it and the pawl longitudinally within the slot 126, thereby extending the pawl end into one of the notches 121 of the ratchet head 123.

Alternatively, the slot 126 can be linear, such that the post member 127 must be held in the retracted position to allow for free rotation of the drive head 115 in either direction.

Figure 2:
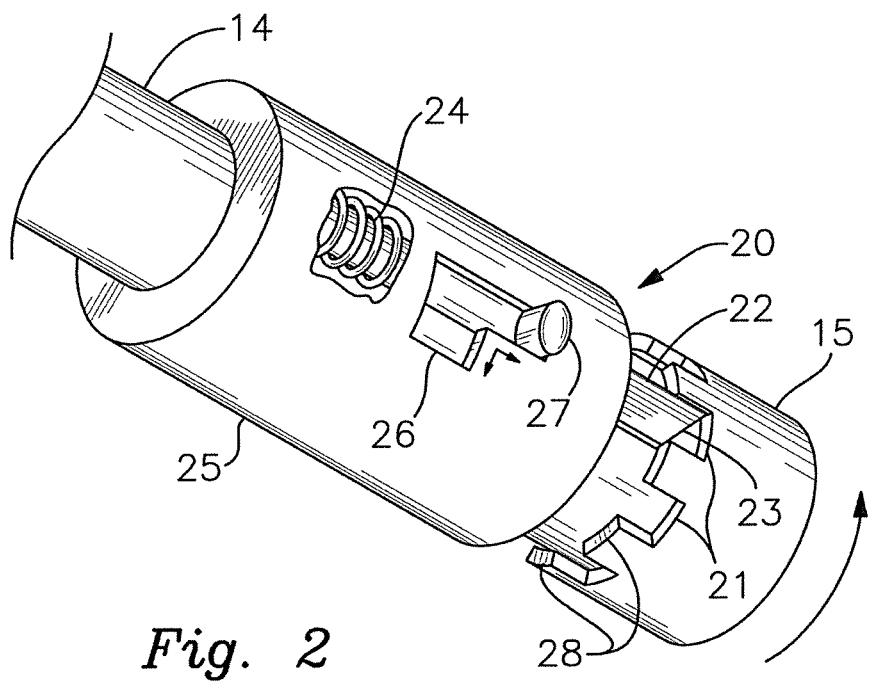
FIG. 2 is a partial view of the prior art device of FIG. 1, better illustrating the quick release disengagement mechanism.
Figure 3:
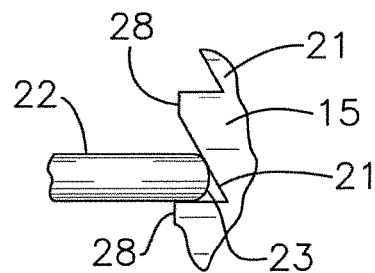
FIG. 3 is a partial view illustrating an alternative prior art ratchet and pawl mechanism.
Figure 4:
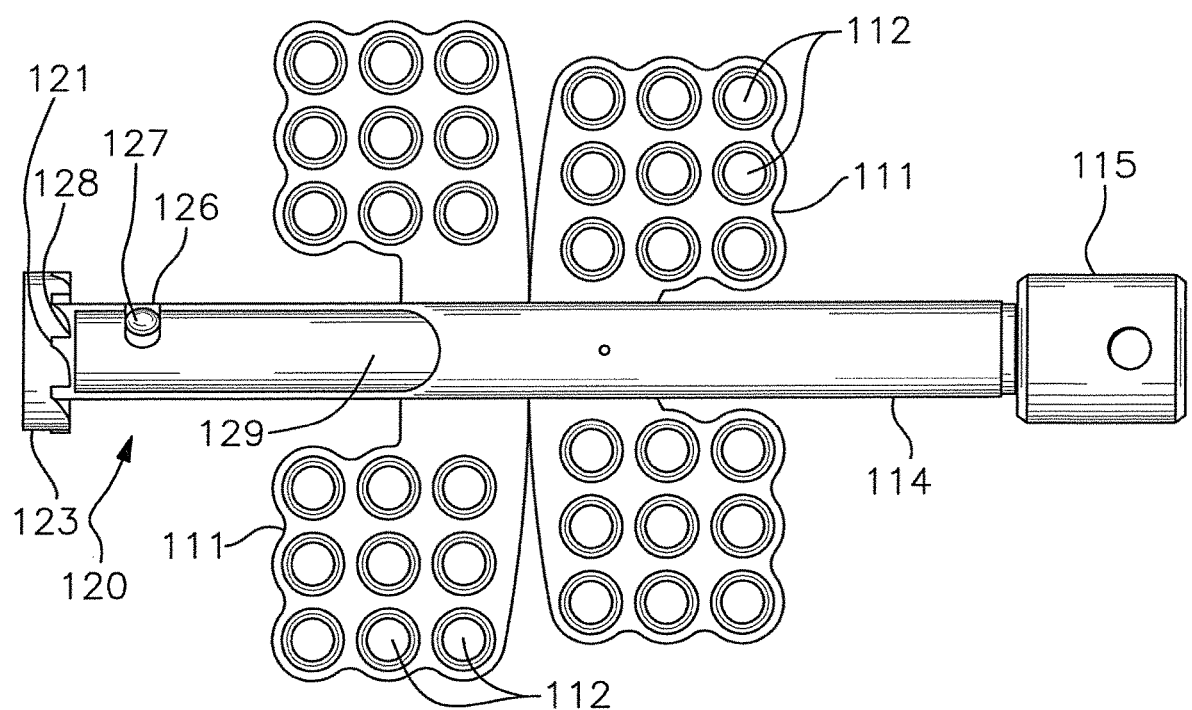
FIG. 4 is a plan view of an illustrative embodiment of a distraction device having a quick release disengagement mechanism wherein the pawl housing is provided with a sloping transition shoulder.
Figure 5:
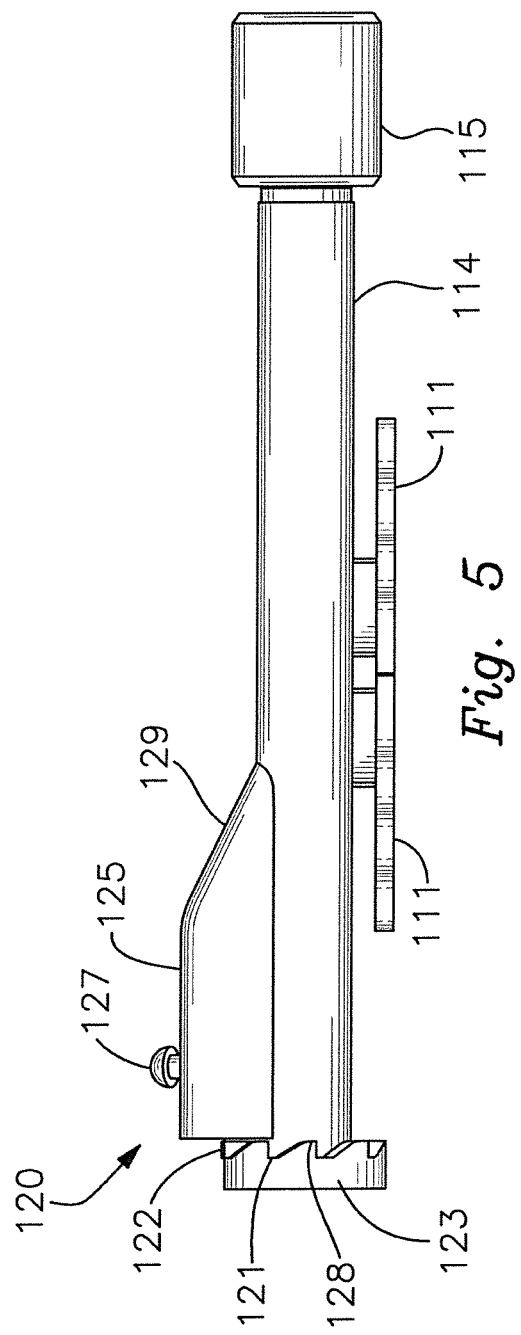
FIG. 5 is a view of the distractor embodiment of FIG. 4 rotated approximately 90 degrees.
Figure 6:
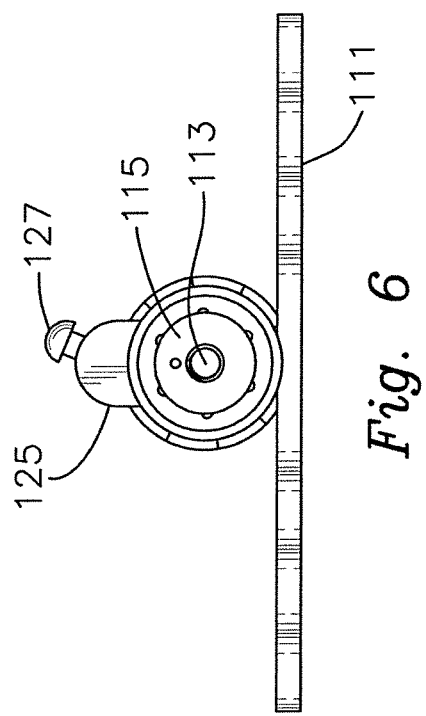
FIG. 6 is an end or axial view of the distractor embodiment of FIG. 4 showing the drive head at the proximal end of the device.
Figure 7:
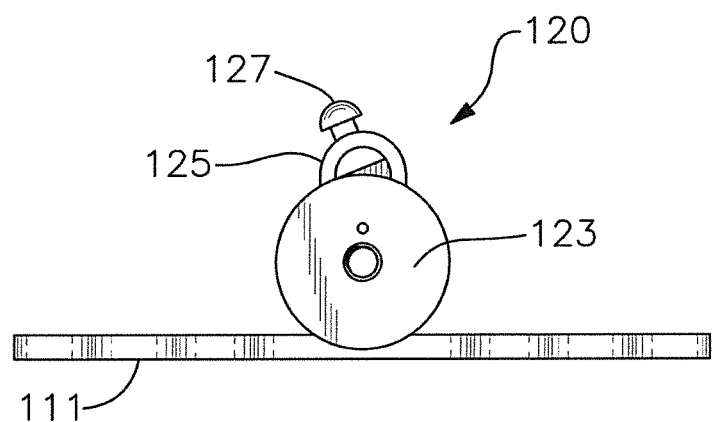
FIG. 7 is an end or axial view of the distractor embodiment of FIG. 4 showing the ratchet head at the distal end of the device.
Figure 8:
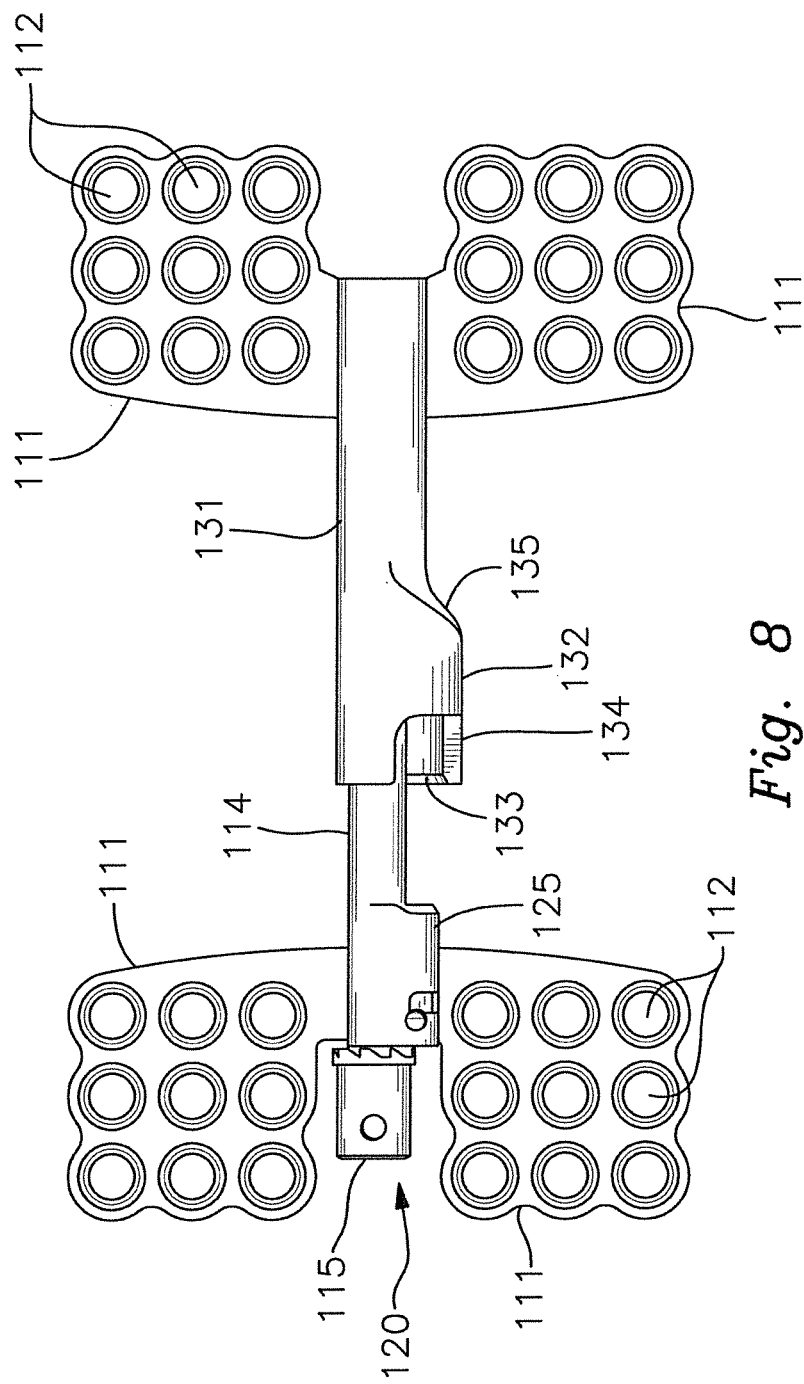
FIG. 8 is a plan view of an alternative embodiment of a distraction device having a quick release disengagement mechanism wherein the enlarged end of the sleeve housing is provided with a sloping transition shoulder.
Figure 9:
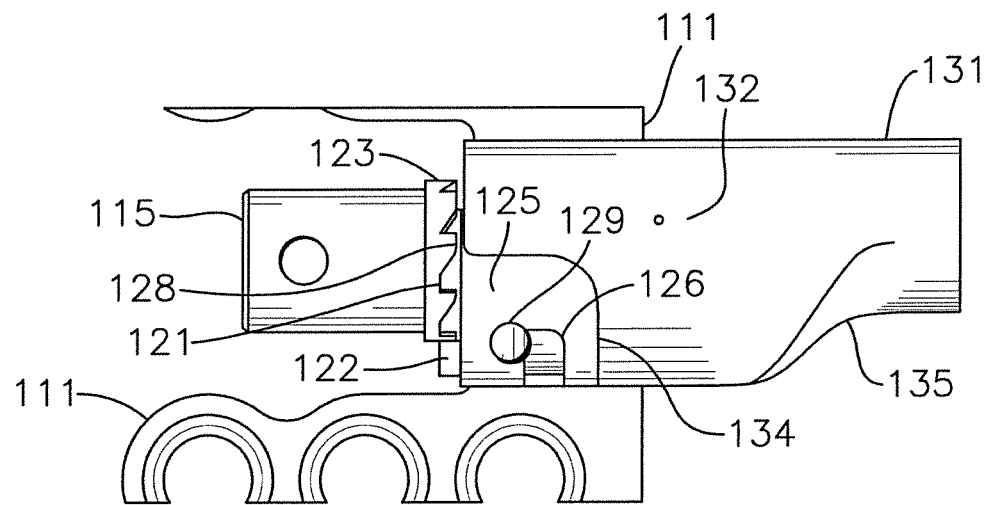
FIG. 9 is a partial illustration of the distractor embodiment of FIG. 8 in the contracted state and showing the ratchet and pawl assembly as received within the enlarged end of the sleeve housing.
Figure 10:
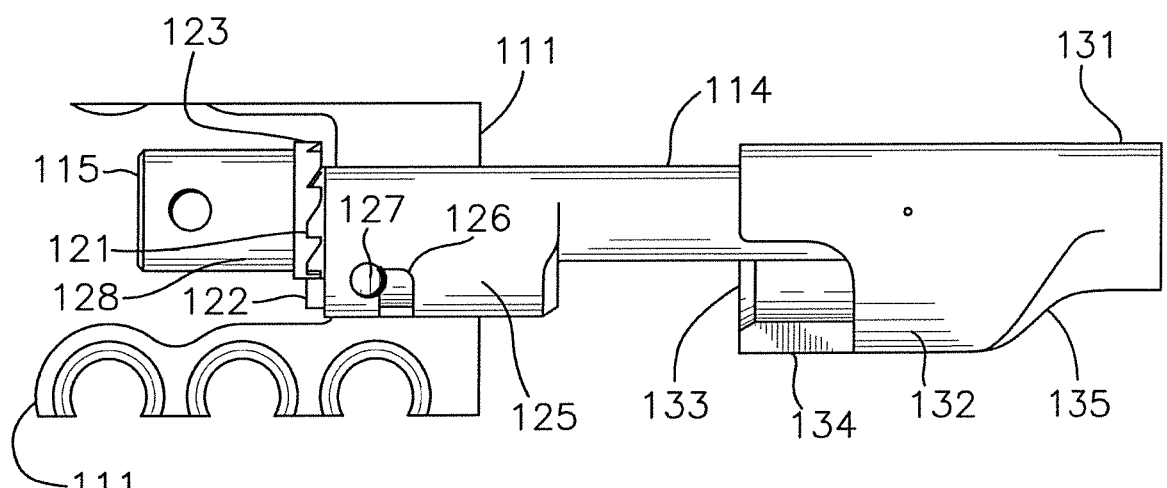
FIG. 10 is a partial illustration of the distractor embodiment of FIG. 8 in the distracted state and showing the enlarged end of the sleeve housing separated from the ratchet and pawl assembly as received.

An alternative and preferred embodiment of the distractor device is illustrated in FIGS. 8 through 10 wherein the distractor device comprises a tubular rod housing 114 and a tubular sleeve housing 131 mated in telescoping manner. In this embodiment the drive head member 115 and the ratchet and pawl assembly 120 are both disposed on the proximal end of the device, the drive head member 115 being connected directly to the ratchet head 123. The linear, elongated rod housing 114 comprises a cylindrical outer surface and the pawl housing 125 extends outwardly from the outer surface of the rod housing 114. Single direction distraction to separate the bone plate members 111 as well as release of the ratchet and pawl assembly 120 to allow for rotation of the drive head in the opposite direction and contraction of the bone plate members 111 operates in known manner as illustrated in prior art FIGS. 1 through 3 and further described above.

A single or paired bone plate member 111 is affixed to or adjacent the proximal end of the rod housing 114 and the pawl housing 125. Another single or paired bone plate member 111 is affixed to or adjacent the distal end of a sleeve housing 131. Sleeve housing 131 is a linear, elongated, tubular member having a bore to receive rod housing 114 in a telescoping manner, such that the distraction device is extended or contracted by rotating the drive head member 115 to cause relative movement between the sleeve housing 131 and rod housing 114, which in turn separates or brings together the bone plate members 111.

The proximal end of the sleeve housing 131 is structured with an enlarged end 132 which defines a pawl housing recess 133 sized and configured such that, as shown in FIG. 9, the pawl housing 125 which extends from the outer surface of the rod housing 114 is received within the pawl housing recess 133 of the enlarged end 132 when the distraction device is in the fully contracted state. A release actuator notch 134 is provided in the enlarged end 132 to accommodate the elongated release actuator or post 127 and to allow access to the release actuator 127 if necessary prior to extension of the distraction device to a distance sufficient for exposure of the release actuator 127. As shown in FIG. 10, rotation of the drive head member 115 to separate the bone plate members 111 results in relative telescoping movement between the sleeve housing 131 and the rod housing 114.

The distal end of the enlarged end 132 is provided with or comprises a rounded, curved or sloping transition shoulder 135, such that the enlarged end 132 does not present an abrupt edge or right angle shoulder against soft tissue as the device is implanted, extended to separate the bone plate members 111, or removed. The sloping transition shoulder 135 diminishes in the distal direction until it smoothly transitions onto the outer surface of the sleeve housing.

In use, one of the bone plate members 111 will be affixed to a stationary bone while the other bone plate member 11 will be affixed to a free piece of bone which is to be distracted. Typically, the distal bone plate member 111 of the sleeve housing 131 is affixed to the stationary bone and the proximal bone plate member 111 adjacent the drive head member 115 and pawl and ratchet assembly 120 is affixed to the free bone, as this orientation provides easier access to the drive head member 115. The orientation can however be reversed.

Figure 11:
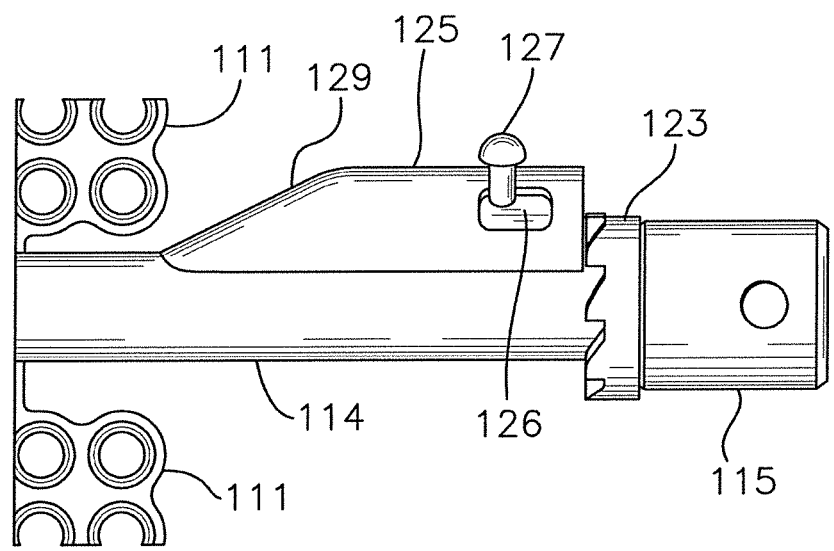
FIG. 11 is a partial illustration of an alternative embodiment of the distractor device wherein the pawl housing having the sloping transition shoulder is disposed on the same end of the device as the drive head member.

Alternatively, the distraction device may be structured as shown in FIG. 11, wherein the pawl housing 125 is provided with a rounded, curving or sloping transition shoulder 129. This construction may be utilized in the embodiment shown in FIGS. 4 through 7 or may be incorporated into the embodiment shown in FIGS. 8 through 10 such that both the enlarged end 132 of the sleeve housing 131 and the pawl housing 125 present sloping transition shoulders 135 and 129, respectfully.

Furthermore, the embodiment shown in FIGS. 4 through 7 may be altered by connecting the drive head 115 to the ratchet head 123 as shown in FIG. 11, thereby reversing the distal and proximal directions while maintaining the operational functionality of the distraction device.

It is understood that equivalents and substitutions for certain elements described above may be obvious to those of skill in the art, and therefore the true scope and definition of the invention is to be as set forth in the following claims.

We claim:

1. A bone distraction device comprising:
a pair of bone plate members;
a threaded rod retained within an elongated, linear rod housing having an outer surface, whereby rotation of said threaded rod within said rod housing in a distraction direction results in relative separation of said bone plate members and rotation of said threaded rod in the opposite direction results in relative contraction of said bone plate members;
a drive head positioned at one end of said rod housing and connected to said threaded rod, whereby rotation of said drive head rotates said threaded rod;
a ratchet head connected to said threaded rod and said drive head, said ratchet head having teeth and notches disposed annularly thereon;
a pawl housing positioned on and extending outwardly from said rod housing, said pawl housing retaining a pawl biased into one of said notches on said ratchet head to define an engaged position, said pawl and said notches configured such that said drive head is rotatable only in said distraction direction when said pawl is in said engaged position;
said pawl housing comprising a sloping transition shoulder diminishing to transition onto said outer surface of said rod housing;
said rod housing having a proximal end and a distal end, wherein said drive head is positioned on said proximal end of said rod housing and said pawl housing is positioned on said distal end of said rod housing, wherein said sloping transition shoulder diminishes in a proximal direction; and
a slot disposed in said pawl housing and a post member connected to said pawl and extending through said slot, said slot having a longitudinal portion and an annularly oriented portion, and whereby said pawl is retracted away from said notches and teeth by moving said post member within said slot longitudinally away from said ratchet head and then annularly to define a disengaged position, such that rotation of said drive head is allowable in either direction when said pawl is in said disengaged position.

2. A bone distraction device comprising:
a pair of bone plate members;
a threaded rod retained within an elongated, linear rod housing having an outer surface;
a drive head positioned at one end of said rod housing and connected to said threaded rod, whereby rotation of said drive head rotates said threaded rod, said drive head having teeth and notches disposed annularly thereon;
a pawl housing positioned on and extending outwardly from said rod housing adjacent said drive head, said pawl housing retaining a pawl biased into one of said notches on said drive head to define an engaged position, said pawl and said notches configured such that said drive head is rotatable only in one direction when said pawl is in said engaged position;
a slot disposed in said pawl housing and a release actuation member connected to said pawl and extending through said slot, said slot having a longitudinal portion and an annularly oriented portion, and whereby said pawl is retracted away from said drive head notches and teeth by moving said release actuation member within said slot longitudinally away from said drive head and then annularly to define a disengaged position, such that rotation of said drive head is allowable in either direction when said pawl is in said disengaged position;
a sleeve housing telescopically mounted on said rod housing, wherein one of said pair of bone plate members is affixed to said rod housing and the other of said pair of bone plate members is affixed to said sleeve housing;
said rod housing having a proximal end and a distal end, wherein said drive head and said pawl housing are positioned on said proximal end of said rod housing;
said sleeve housing having a proximal end and a distal end, said sleeve housing further comprising an enlarged end at the proximal end of said sleeve housing, said enlarged end comprising a pawl housing recess sized and configured to receive said pawl housing therein;
whereby rotation of said threaded rod within said rod housing in the distraction direction results in lengthening of said bone distraction device and relative separation of said bone plate members and rotation of said threaded rod in the opposite direction results in shortening of said bone distraction device and relative contraction of said bone plate members.

3. The bone distraction device of claim 2, said enlarged end of said sleeve housing further comprising a release actuation notch such that said release actuator remains accessible when said pawl housing is received within said pawl housing recess.

4. The bone distraction device of claim 2, said enlarged end comprising a sloping transition shoulder diminishing to transition onto said outer surface of said sleeve housing in a distal direction.

5. The bone distraction device of claim 3, enlarged end comprising a sloping transition shoulder diminishing to transition onto said outer surface of said sleeve housing in a distal direction.

6. The bone distraction device of claim 2, said pawl housing comprising a sloping transition shoulder diminishing to transition onto said outer surface of said rod housing in a distal direction.

7. The bone distraction device of claim 3, said pawl housing comprising a sloping transition shoulder diminishing to transition onto said outer surface of said rod housing in a distal direction.

8. The bone distraction device of claim 4, pawl housing comprising a sloping transition shoulder diminishing to transition onto said outer surface of said rod housing in a distal direction.

9. The bone distraction device of claim 5, said pawl housing comprising a sloping transition shoulder diminishing to transition onto said outer surface of said rod housing in a distal direction.

\* \* \* \* \*

UNITED STATES PATENT AND TRADEMARK OFFICE
CERTIFICATE OF CORRECTION

| | |
|---|---|
| PATENT NO. | : 11,399,871 B2 |
| APPLICATION NO. | : 16/448340 |
| DATED | : August 2, 2022 |
| INVENTOR(S) | : Heinz Staehler and Thomas S. Johnston, Jr. |

It is certified that error appears in the above-identified patent and that said Letters Patent is hereby corrected as shown below:

On the Title Page

Please add item (73) Assignee: KLS MARTIN, L.P., Jacksonville, FL (US)

Signed and Sealed this
Sixth Day of June, 2023

Katherine Kelly Vidal
*Director of the United States Patent and Trademark Office*